(12) United States Patent
Lord et al.

(10) Patent No.: US 9,023,299 B2
(45) Date of Patent: May 5, 2015

(54) REACTOR

(75) Inventors: Edward Adrian Lord, London (GB); Arthur James Reason, Thornaby (GB)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 13/583,335

(22) PCT Filed: Jan. 12, 2012

(86) PCT No.: PCT/GB2012/050056
§ 371 (c)(1), (2), (4) Date: Sep. 21, 2012

(87) PCT Pub. No.: WO2012/110775
PCT Pub. Date: Aug. 23, 2012

(65) Prior Publication Data
US 2014/0024863 A1    Jan. 23, 2014

(30) Foreign Application Priority Data
Feb. 14, 2011  (GB) .................................. 1102551.7

(51) Int. Cl.
| | |
|---|---|
| B01J 8/04 | (2006.01) |
| C07C 29/14 | (2006.01) |
| C10G 45/44 | (2006.01) |
| C10G 3/00 | (2006.01) |
| C07C 7/163 | (2006.01) |
| C10G 49/00 | (2006.01) |
| C10G 45/32 | (2006.01) |
| B01J 19/24 | (2006.01) |
| C07C 29/141 | (2006.01) |
| C10G 2/00 | (2006.01) |

(52) U.S. Cl.
CPC ....... *B01J 19/248* (2013.01); *C10G 2300/1096* (2013.01); *C10G 45/44* (2013.01); *C10G 3/42* (2013.01); *C07C 7/163* (2013.01); *C10G 49/002* (2013.01); *C10G 45/32* (2013.01); *B01J 2219/00024* (2013.01); *C10G 2300/4081* (2013.01); *C07C 29/141* (2013.01); *B01J 8/0465* (2013.01); *B01J 2208/00265* (2013.01); *C10G 2/32* (2013.01); *Y10S 585/903* (2013.01)

(58) Field of Classification Search
USPC ......... 422/620, 621, 622, 632, 634, 635, 636, 422/642, 644; 585/259, 260, 265, 266, 903; 568/881
See application file for complete search history.

(56) References Cited

U.S. PATENT DOCUMENTS

| | | |
|---|---|---|
| 3,976,713 A | 8/1976 | Holmes et al. |
| 4,681,674 A | 7/1987 | Graven et al. |
| 4,704,492 A | 11/1987 | Nemet-Mavrodin |

(Continued)

FOREIGN PATENT DOCUMENTS

GB          1315217           5/1973

OTHER PUBLICATIONS

Mohundro, Edgar L., "Overview on C2 and C3 Selective Hydrogenation in Ethylene Plants," AIChE 15th Ethylene Producers Conference 2003, Session 64a, p. 560, Figure 7.

*Primary Examiner* — Lessanework Seifu
(74) *Attorney, Agent, or Firm* — Armstrong Teasdale LLP

(57) ABSTRACT

A liquid/gas reactor includes a bulk catalyst bed and means for supplying fresh feed and recycled at least partially converted liquid product stream to the bulk catalyst bed. The reactor also includes means for collecting an at least partially converted liquid product stream from the bulk catalyst bed and recycling at least a portion thereto. A minor catalyst bed extends substantially vertically through the bulk catalyst bed. Means for supplying recycled at least partially converted product stream only to the minor catalyst bed is also provided. A separating wall is disposed between the bulk catalyst bed and the minor catalyst bed.

15 Claims, 2 Drawing Sheets

(56) References Cited

U.S. PATENT DOCUMENTS

| | | |
|---|---|---|
| 4,937,051 A | 6/1990 | Graven et al. |
| 4,960,960 A | 10/1990 | Harrison et al. |
| 5,573,736 A | 11/1996 | Jubin, Jr. |
| 6,693,225 B2 | 2/2004 | Boyer et al. |
| 7,663,006 B2 | 2/2010 | Oota et al. |
| 2006/0135830 A1 | 6/2006 | Birkhoff et al. |

REACTOR

The present invention relates to a liquid/gas reactor. More particularly, the present invention relates to a liquid/gas reactor which facilitates the control of temperature in the reactor. The invention also relates to a process carried out in said reactor.

Chemical reactions between liquids and gases are often carried out over a solid catalyst bed. The reaction may be exothermic, i.e. it generates heat, or it may be endothermic, i.e. it utilises heat and cooling is noted. In some reactions heat effects of the reaction are moderate although even in these, if the temperature is not controlled, a loss of selectivity may result. However, for more exothermic or endothermic reactions it is necessary to be more rigorous in controlling the heat effects. In extreme cases, the heat generated by strongly exothermic reactions can lead to thermal runaway. Similarly the cooling effects of strongly endothermic reactions can lead to quenching of the reaction.

A commonly used method of controlling temperature in a liquid/gas reactor in which an exothermic or endothermic reaction occurs is by recycle of heated or cooled product. The recycle has the effect of limiting the temperature rise. These so-called "Liquid Recycle" reactors are in widespread commercial use, for example, in the hydrogenation of benzene, the selective hydrogenations of olefins to remove alkynes and/or dienes and in the hydrogenation of aldehydes to alcohols.

A typical scheme for the selective hydrogenation of alkynes and dienes in $C_2$ and $C_3$ streams is illustrated in FIG. 1. This arrangement is similar to that illustrated in a presentation to AIChE 15$^{th}$ Ethylene Producers Conference 2003, Session 64a "*Overview on $C_2$ and $C_3$ Selective Hydrogenation*" page 560, FIG. 7. The hydrogenation unit comprises a main reactor 1 and a finishing reactor 2. $C_3$ feedstock is supplied in line 3 to the main reactor 1 where it is reacted over a catalyst with hydrogen that has been supplied in line 4. Product is extracted in line 5 and cooled in cooler 6 before being passed in line 7 to liquid/gas separator 8. A proportion of the liquid is removed in line 9 and recycled to the main reactor 1. In the illustrated arrangement the recycle stream 9 is combined with the feedstock stream 3 before being supplied to the main reactor 1.

The excess gas from the separator is removed in line 10.

The remaining liquid from the gas/liquid separator is removed in line 11 and fed to the finishing reactor 2. This reactor is a plug flow reactor. Product is removed in line 12. It will be understood that the Liquid Recycle reactor is partially back-mixed since the feed is diluted with the recycled product stream.

In the case of hydrogenation of 100% alkene to alkane or of aldehyde to alcohol, typically recycle rates of 10 to 20 times the feed rate are needed in order to avoid the temperature rise over the reactor being above 20° C. This recycled product significantly dilutes the reactant and consequently the conversion achieved in the Liquid Recycle reactor is reduced.

The finishing reactor 2, which may also be known as a polishing reactor, is needed to make a high quality product which has low levels of unreacted feed components. In order to have liquid velocities suitable for good distribution the cross-sectional area of the finishing stage has to be much smaller than the Liquid Recycle reactor and thus in order to achieve adequate catalyst volume a long finishing reactor must be used.

A schematic illustration of another example of a Liquid Recycle reactor of the prior art is illustrated in FIG. 2. Here gas feed is added in line 21 to the reactor 22. Fresh feed is added in line 23 and mixed with recycled product from line 24 before being supplied in line 25 into the headspace of the reactor 21. The mixed liquid and gas then flow downwardly through the catalyst bed 26 where reaction occurs. Unreacted gas is removed in line 27 and a proportion of the product is removed in line 28. The remainder of the product stream is removed in line 29 by pump 30 before being heated or cooled in heater/cooler 31 to the desired temperature before being recycled to reactor 22 in line 24.

U.S. Pat. No. 6,693,225 describes a liquid recycle reactor with more than one catalyst bed in which hydrogen is added to the first bed and between the beds. Optionally a second external plug flow reactor is added to complete the conversion.

An alternative arrangement is described in U.S. Pat. No. 4,704,492 which relates to the selective hydrogenation of acetylenic impurities in crude butadiene and U.S. Pat. No. 4,937,051 which relates to the hydrogenation of hydrocarbon oils. In these cases a succession of beds with liquid recycle from final product to the entry to the first bed and other recycles from bed outlets to bed inlets are described. Hydrogen is added between beds to improve selectivity. A second external finishing/polishing stage is often required in order to get high efficiency and/or high-quality product. The first recycle reactor is used to provide uniformity of reaction conditions and good vapour/liquid mixing. However, it suffers from the drawback of inefficient utilization of catalyst since it is inherently partially back-mixed.

As explained in U.S. Pat. No. 7,663,006, high liquid velocities are required to achieve good vapour/liquid contact in these packed bed reactors. In GB 1315217 a process for the hydrogenation of aldehydes is described in which a high liquid flow is used to achieve good catalyst utilisation. An alternative arrangement is described in U.S. Pat. No. 4,681,674. Here recirculation is recommended in order to keep uniform catalyst wetting. However, this process suffers from the disadvantage that recirculation of product to the feed dilutes the reactant and reduces reaction rate.

In U.S. Pat. No. 5,573,736 a reactor is described which is made up of a series of separate zones all with liquid recirculation in order to remove reaction heat. A final bed in the reactor is plug flow with no liquid recirculation. In a design of this type, the velocity in the final plug flow section will be very low due to the relatively low liquid rate and therefore vapour/liquid distribution is likely to be poor.

A process in which hydrogenation is carried out in two stages, either in one reactor or using two reactors in series, is described in U.S. Pat. No. 4,960,960. The second stage is described as a separate reactor with or without liquid recycle or as a bed of the same diameter as the main bed placed below the main bed. The design suffers from the disadvantage of requiring a second vessel or requiring increased reactor height in a section of reduced liquid velocity; reducing the liquid velocity leads to inefficient catalyst utilisation.

It has now been found that by a modification of the packed bed reactor it is possible to approximately double the effectiveness of the catalyst. This can be used to give a higher quality product and may make it possible to dispense with the finishing reactor. Even if the finishing reactor is maintained there will still be a reduction in plant and catalysts costs thereby improving the economics of the process.

According to the present invention there is a provided a liquid/gas reactor comprising:
  (a) a bulk catalyst bed and means for supplying fresh feed and recycled at least partially converted liquid product stream to said bulk catalyst bed;

(b) means for collecting an at least partially converted liquid product stream from said bulk catalyst bed and recycling at least a portion thereof to step (a);

(c) a minor catalyst bed extending substantially vertically through the bulk catalyst bed and means for supplying recycled at least partially converted product stream only to said minor catalyst bed; and (d) a separating wall between said bulk and said minor catalyst bed.

Gaseous reactant and fresh liquid feed are generally supplied to the bulk catalyst bed in step (a)

The reactor of the present invention will generally be suitable for use with an exothermic or endothermic reaction With the arrangement of the present invention, the minor catalyst bed is supplied only with feed which has already been subjected to the reaction and therefore will be at least partially converted. Thus the stream exiting the minor catalyst bed will provide a more-fully converted final product than in a reactor without the minor catalyst bed.

The minor catalyst bed may be in any suitable location in the bulk catalyst bed but may, in one arrangement, be located such that it is central thereto such that the bulk catalyst bed forms on annulus therearound.

Any suitable ratio of catalyst area of the minor catalyst bed to the bulk catalyst bed may be used. Generally the ratio will be selected to preserve the required vapour/liquid mixing and achieve the required wetting of the catalyst. Preferably the ratio of the minor catalyst bed to the bulk catalyst bed will be from about half to about twice the ratio of the flowrates of recycle to the minor bed to the feed plus the recycle to the bulk bed. In one arrangement the ratio will be substantially 1:1. This means that the minor catalyst bed will have a liquid velocity which gives good vapour/liquid mixing and good wetting. Generally this will be of the same level as that achieved in the bulk catalyst bed.

In one arrangement the reactor bottoms from the bulk catalyst bed will all be recycled with a portion being recycled to the bulk catalyst bed and a portion being passed to the minor catalyst bed.

The flowrate to the minor catalyst bed is preferably equal to the final product rate although for ease of control an excess of up to 100% may be used with the excess being joined with the recycle from the bulk catalyst bed.

The reactor will preferably include a heater or cooler to adjust the temperature of the recycle stream.

With the arrangement of the present invention, improved conversion can be obtained. In some arrangements the need for a separate polishing reactor is obviated. This reduces capital and operating costs.

Any suitable catalyst may be used. Generally, the selection if the catalyst will depend on the reaction to be carried out. The catalyst may be of any suitable form. Examples include pellets, extrudates, resins or impregnated packing. Examples of catalysts used include nickel, copper/chromium or palladium. Suitable supports include alumina. The same or different catalysts may be used in the bulk and minor catalyst beads. The catalyst located in the minor catalyst bed and the bulk catalyst bed may be the same or different.

The reactor can be constructed of any suitable materials. The temperature at which the beds are operated may be the same or different. Where they are different the reactor will include heating or cooling means. Where the beds are to be operated at different temperatures the separation wall between the two beds will be fabricated from insulating material.

The separating wall may be of any suitable structure. In one arrangement it may simply be an internal pipe in which the minor catalyst bed will be located. The pipe may be of any suitable cross-section but may be of circular cross-section. In one alternative arrangement the separation wall will be formed by, for example, a half pipe fastened to the wall of the reactor.

A particular advantage of the present invention is that existing single or multiple bed reactors can be modified to have the vertical minor bed installed. Whether the reactor is newly fabricated or a modification of an existing reactor, where there are multiple beds, the minor catalyst bed can be provided on one, some or all of the beds.

The apparatus of the present invention can be used for any exothermic or endothermic liquid/gas reaction over a solid catalyst bed. Examples of exothermic reactions include hydrogenations of aldehydes, ketones, alkynes, dienes, or aryl compounds and oxidations. Examples of endothermic reactions include dehydrogenations. In particular the present invention is suitable for the selective hydrogenation of butadiene to butene, the production of cyclohexane from benzene or the production of 2-ethyl hexanol from 2-ethyl-hex-2-enal.

Thus according to a second aspect of the present invention there is provided a process for a gas/liquid reaction comprising the steps of:

(a) supplying feed comprising fresh feed and recycle product stream to the bulk catalyst bed of the apparatus of the above-mentioned first aspect;

(b) supplying gas to the reactor of the above-mentioned first aspect;

(c) allowing reaction to occur in the bulk catalyst bed;

(d) collecting an at least partially converted liquid product steam;

(e) recycling at least a portion of said partially converted liquid product stream to the bulk catalyst bed;

(f) supplying at least a portion of said partially converted liquid product stream to the minor catalyst bed of the above-mentioned first aspect of the present invention;

(g) allowing reaction to occur in the minor catalyst bed; and (h) collecting the product stream from the minor catalyst bed.

Whilst all of the partially reacted stream from the bulk catalyst bed may be returned to the reactor either as recycle to the bulk catalyst bed or as feed to the minor catalyst bed, it will be understood that some of the partially reacted stream may be collected and recovered.

The partially reacted stream returned to the reactor may be heated or cooled as required before being recycled.

The preferred flow regime will generally be such as to give a positive pressure drop. However, low liquid rate or trickle-flow beds may also be used. Where a liquid/gas distributor is to be used, it may be of any suitable design.

The apparatus and process of the present invention is generally applicable to downflow systems. However, it may also be applied to upflow systems and systems which use a large excess of gas. In one arrangement, the gas and liquid streams may be in co-current downflow. The apparatus and process of the present invention may be used in exothermic and endothermic reactions.

The process of the present invention may be any suitable reaction. In one arrangement, the reaction may be the hydrogenation of an aldehyde to alcohol. In another arrangement, the reaction may be the selective hydrogenation of a diene, such as butadiene, or an alkyne, to an olefin. In a further arrangement, the reaction may be the hydrogenation of the aromatic ring in an aromatic compound.

The catalyst selected and the reaction conditions will depend on the process being carried out. For example, where the reaction is the hydrogenation of an aldehyde, a copper/ chrome catalyst may be used and the reaction may be carried out at a temperature of from about 140° C. to about 200° C. and a pressure above 10 barg. For the selective hydrogenation of dienes, palladium or alumina catalyst may be used and the reaction may be carried out at temperatures of from about 20° C. to about 130° C. and a pressure of from about 5 barg to about 20 barg.

The present invention will now be described, by way of example reference to the following drawings in which.

Figure 1:
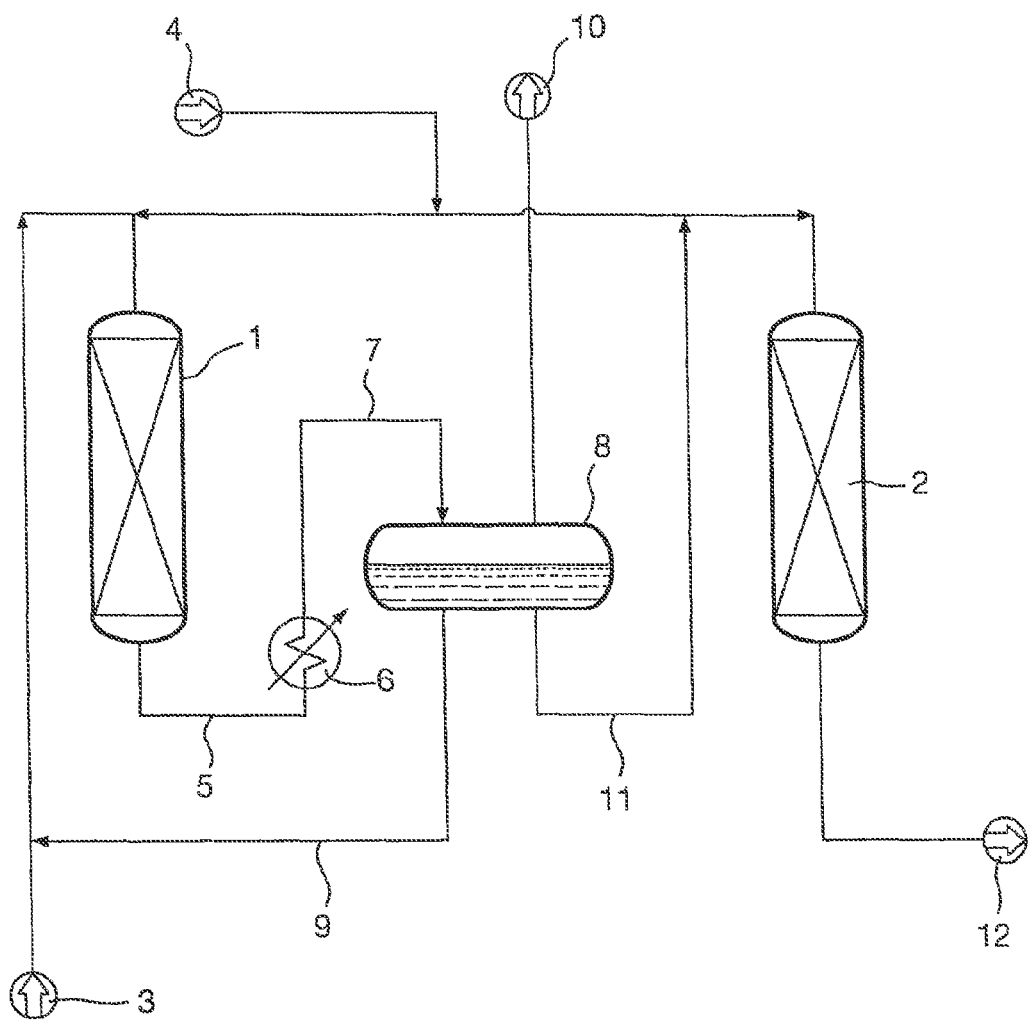
FIG. 1 is a schematic flowsheet for a reactor system of the prior art.
Figure 2:
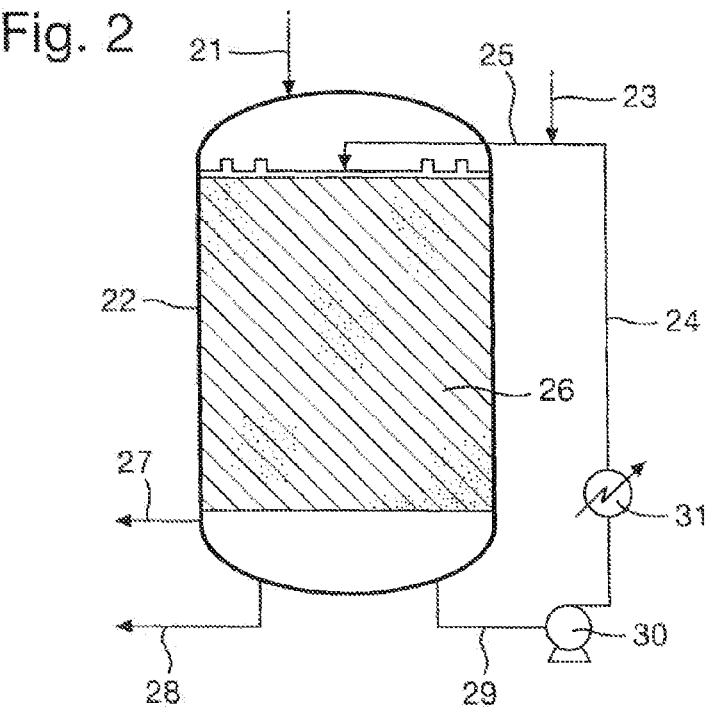
FIG. 2 is a schematic diagram of a liquid/gas reactor of the prior art.
Figure 3:
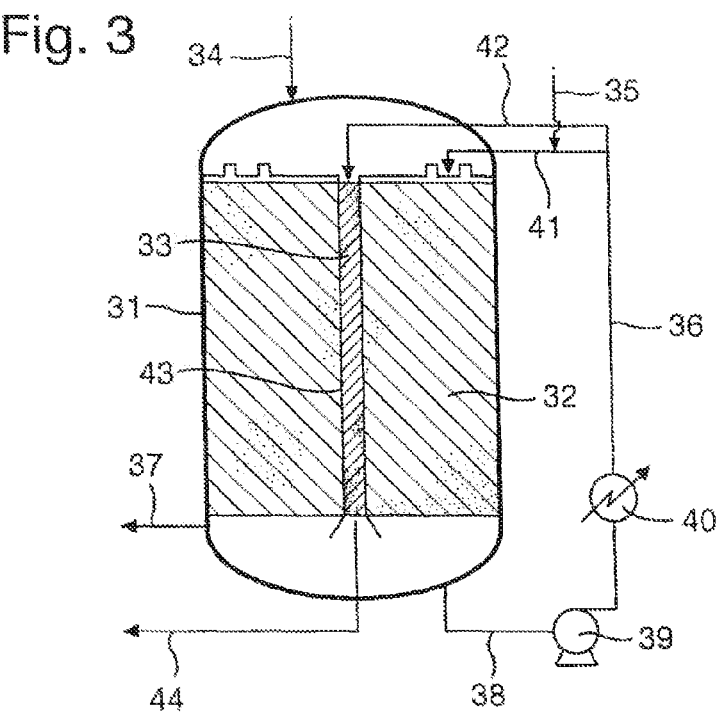
FIG. 3 is a schematic representation of the apparatus of the present invention.

The apparatus of the present invention is illustrated in FIG. 3. The reactor vessel 31 comprises a bulk catalyst bed 32 and a minor catalyst bed 33. The gas is fed in line 34. Fresh feed is supplied in line 35 where it is mixed with recycled partially reacted stream recycled in line 41. This mix of fresh feed and partially reacted stream is fed to the bulk catalyst bed 32 where reaction with the gas occurs. Offgas is removed in line 37 and the partially reacted product stream is recovered in line 38 using pump 39 before having the temperature adjusted by heater or cooler 40. This temperature adjusted stream 36 is split with stream 41 being mixed with fresh feed 35 before being supplied to the bulk catalyst bed 32. The remainder is passed in line 42 to the minor catalyst bed 33 which is separated from the bulk catalyst bed 32 using separation wall 43. This stream is subjected to the further reaction with the gas supplied in line 34. Product from the minor catalyst bed is collected in line 44. This will have improved conversion when compared to that achieved in conventional liquid recycle reactors.

The reactor of the present invention may be used in the hydrogenation of aliphatic $C_2$-$C_{20}$ aldehydes to the corresponding alcohol over a CuCr catalyst. The same catalyst will generally be used in both catalyst beds. In this reaction, the residence time, based on feed, will be about 0.1 to about 10 hours. The temperature of the catalyst beds will be in the region of about 100° C. to about 200° C. at pressures of about 5 to about 50 bar. Alternatively, the reaction may be carried out over a nickel catalyst in which case the residence time, based on feed, will be about 0.1 to about 10 hours. The reaction will be carried out at temperatures of from about 70° C. to about 150° C. at pressures of from about 5 to about 50 bar.

The recycle rate will generally be selected to be similar or the same as that that used in prior art processes. Without wishing to be bound by any theory, it is believed that the recycle is required in order to restrict the temperature rise. By limiting the temperature rise, the outlet temperature can be limited. This has the benefit of limiting, or avoiding, by-product formation and may provide improved selectivity. In addition this avoids a low inlet temperature. This is beneficial since a low inlet temperature would require a large induction zone in the reactor inlet before the reaction could start. However, the recycle rate should not be larger than necessary as this unduly dilutes the reactants with product and reduces the effectiveness of the catalyst.

Whichever catalyst system is used the recycle rates will be between about 5 to about 50 times the feed rate. The catalyst beds will be sized so that the liquid superficial velocity is in the range of about 0.2 to about 4 cm/s. The hydrogen will generally be fed at quantities of approximately equal to or up to about double the stoichiometric requirement. Since this reaction is an exothermic reactor a cooler 40 will be used to remove the heat of the reaction.

COMPARATIVE EXAMPLES 1 AND 2 n-Nonaldehyde was passed over a bed of nickel catalyst at 50 barg with 2% excess hydrogen. Using $C_{out}/C_{in}=e^{-k/LHSV}$ the first order kinetic coefficient k can be calculated. Since substantially the same value is obtained for both examples it will be seen that a first order model is a good prediction of conversion. The conditions and results are set out in Table 1.

TABLE 1

|  | Comparative Example 1 | Comparative Example 2 |
|---|---|---|
| Feed l/h | 0.4 | 0.4 |
| Recycle l/h | 6 | 4.8 |
| Recycle: Feed | 15.00 | 12.00 |
| Mixed feed + recycle nonanal wt % | 6.5 | 7.8 |
| Catalyst volume l | 0.40 | 0.40 |
| LHSV (based on feed + recycle) h$^{-1}$ | 16.00 | 13.00 |
| Reactor Temperature ° C. | 120 | 120 |
| Residual Nonanal wt % | 0.27 | 0.14 |
| $C_{out}/C_{in}$ | 0.04 |  |
| Calculated first order kinetic factor hr$^{-1}$ | 51 | 52 |

COMPARATIVE EXAMPLE 3 AND EXAMPLE 4

To illustrate the improvement obtained by using a segregated reactor of the present invention, the catalyst bed is divided between the Main Bed and a second plug flow bed so that the residence time and therefore the conversion $C_{out}/C_{in}$ will be the same as in the comparative examples. Conversion is calculated by $C_{out}/C_{in}=e^{-k/LHSV}$. Details and results are set out in Table 2.

TABLE 2

|  | Comparative Example 3 Single Bed | Example 4 Calculated Performance of Segregated Reactor of Same Volume | | Single Bed Reactor to Equal Performance of Segregated Reactor Single Bed |
|---|---|---|---|---|
|  |  | Main Bed | Plug Flow Bed |  |
| Feed l/h | 0.4 | 0.4 | 0.4 | 0.4 |
| Recycle l/h | 6 | 5.6 |  | 5.44 |
| Mixed feed + recycle nonanal wt % | 6.5 | 6.9 | 0.3 | 6.9 |
| Catalyst volume litre | 0.4 | 0.375 | 0.025 | 0.73 |
| LHSV (based on feed and recycle) h$^{-1}$ | 16.00 | 16.00 | 16.00 | 8.1 |
| Inlet temperature ° C. | 120 | 120 | 120 | 120 |
| Residual Unreacted nonanal wt % | 0.27 | 0.3 | 0.012 | 0.012 |
| $C_{out}/C_{in}$ | 0.04 | 0.04 | 0.04 | 0.002 |

The partitioned bed reactor of the present invention achieves a only 0.012 wt % of residual unreacted nonanal compared to 0.27 wt % with the same volume in a conventional liquid recycle reactor. Thus it will be understood that improved conversion has been achieved.

To achieve the same improvement in performance using a single conventional liquid recycle bed an increased in bed volume of 85% is needed i.e. from 0.4 to 0.73 liters.

The invention claimed is:

1. A liquid/gas reactor comprising:
   (a) a bulk catalyst bed and means for supplying fresh feed and recycled at least partially converted liquid product stream to said bulk catalyst bed;
   (b) means for collecting an at least partially converted liquid product stream from said bulk catalyst bed and recycling at least a portion thereof to step (a);
   (c) a minor catalyst bed extending substantially vertically through the bulk catalyst bed and means for supplying recycled at least partially converted product stream only to said minor catalyst bed; and
   (d) a separating wall between said bulk and said minor catalyst bed.

2. A reactor according to claim 1 wherein the minor catalyst bed is located such that it is central to the bulk catalyst bed which forms on annulus therearound.

3. A reactor according to claim 1 wherein all of the partially converted product stream is recycled with a portion being recycled to the bulk catalyst bed and a portion being passed to the minor catalyst bed.

4. A reactor according to claim 1 wherein the reactor additionally includes a heater or cooler on the recycled, at least partially converted, liquid product stream.

5. A reactor according to claim 1 wherein the beds are operated at different temperatures.

6. A reactor according to claim 5 wherein the separation wall is fabricated from insulating material.

7. A reactor according to claim 1 wherein the ratio of the minor catalyst bed to the bulk catalyst bed will be from about half to about twice the ratio of the flowrates of recycle to the minor bed to the feed plus the recycle to the bulk bed.

8. A reactor according to claim 7 wherein the ratio is substantially 1:1.

9. A reactor according to claim 1 where the catalyst in the minor catalyst bed is different to the catalyst in the major catalyst bed.

10. A process for a gas/liquid reaction comprising the steps of:
    (a) supplying feed comprising fresh feed and recycle product stream to the bulk catalyst bed of claim 1;
    (b) plying gas to the reactor of claim 1;
    (c) allowing reaction to occur in the bulk catalyst bed;
    (d) collecting an at least partially converted liquid product steam;
    (e) recycling at least a portion of said partially converted liquid product stream to the bulk catalyst bed;
    (f) supplying at least a portion of said partially converted liquid product stream to the minor catalyst bed of claim 1;
    (g) allowing reaction to occur in the minor catalyst bed; and
    (h) collecting the product stream from the minor catalyst bed.

11. The process according to claim 10 wherein the partially reacted stream returned to the reactor is heated or cooled before being recycled.

12. The process according to claim 10 for the hydrogenation of an aldehyde to alcohol.

13. The process according to claim 10 for the selective hydrogenation of a diene or an alkyne to an olefin.

14. The process according to claim 13 wherein the diene is butadiene.

15. The process according to claim 10 for the hydrogenation of the aromatic ring in an aromatic compound.

* * * * *